United States Patent [19]
Ueno et al.

[11] Patent Number: 5,163,432
[45] Date of Patent: Nov. 17, 1992

[54] CATHETER TYPE LASER ILLUMINATING APPARATUS

[75] Inventors: Shinichiro Ueno, Sagamihara; Masahiko Hashimoto, Tokyo; Akihisa Adachi, Kawasaki, all of Japan

[73] Assignee: Matsushita Electric Industrial Co., Ltd., Osaka, Japan

[21] Appl. No.: 729,761

[22] Filed: Jul. 15, 1991

[30] Foreign Application Priority Data

Jul. 16, 1990 [JP] Japan .................................. 2-189084
Sep. 27, 1990 [JP] Japan .................................. 2-259674

[51] Int. Cl.⁵ .............................................. A61B 8/12
[52] U.S. Cl. ................... 128/660.03; 606/7; 606/11; 606/12
[58] Field of Search ................. 128/660.03; 606/7, 11, 606/12

[56] References Cited

U.S. PATENT DOCUMENTS

| | | | |
|---|---|---|---|
| 4,576,177 | 3/1986 | Webster, Jr. | 128/660.03 |
| 4,587,972 | 5/1986 | Morantte, Jr. | 128/660.03 |
| 4,887,605 | 12/1989 | Angelson et al. | 128/660.03 |
| 5,029,588 | 7/1991 | Yock et al. | 128/600.03 |

FOREIGN PATENT DOCUMENTS 9101687 2/1991 World Int. Prop. O. ............ 606/12

*Primary Examiner*—Kyle L. Howell
*Assistant Examiner*—J. R. Jastrzab
*Attorney, Agent, or Firm*—Lowe, Price, LeBlanc & Becker

[57] ABSTRACT

A catheter type laser illuminating apparatus for thermally removing an atheroma generated in a blood vessel. The illuminating apparatus comprises a catheter arranged to be inserted into a blood vessel, the catheter being equipped with an ultrasonic transducer for transmitting and receiving an ultrasonic wave to generate an electric signal corresponding to the reception ultrasonic wave. The catheter is further equipped with a laser transmission fiber for emitting the laser light. Also included in the illumination apparatus is a M-mode image producing section for producing an image representative of the dimension of the atheroma on the basis of the electric signal from the ultrasonic transducer. The image is displayed on a CRT in a corresponding relation to an illumination condition of the laser light to the atheroma which is at least one of an illumination time and an illumination power.

8 Claims, 5 Drawing Sheets

CATHETER TYPE LASER ILLUMINATING APPARATUS

BACKGROUND OF THE INVENTION

The present invention relates generally to laser illuminating apparatus, and more particularly to a catheter type laser illuminating apparatus, equipped with a diagnostic ultrasonic transducer and a medical-treatment laser transmission fiber. In use, the apparatus is inserted into an artery blood vessel so as to thermally melt, or remove, an atheroma which narrows or closes the blood vessel.

A catheter type laser illuminating apparatus, disclosed in "O Plus E" No. 109, P75-81, 1988, PO63-3834, will be described hereinbelow with reference to FIG. 1. In FIG. 1, a catheter 51 includes an inside hole 52 for injecting a transparent flush agent, an endscope fiber 53, a laser transmission fiber 54, and a balloon 55 on the exterior of the catheter. Characters A and B represent a blood vessel and an atheroma, respectively. In operation, the catheter 51 is first inserted into the blood vessel A and moved so that its top or distal portion is positioned at the vicinity of the atheroma B. Secondly, the balloon 55 is inflated in order to stop the flow of the blood, and a transparent flush agent such as a physiological brine is injected through the injection hole 52 into the blood vessel A. Thereafter, the endscope fiber 53 is used in order to check the position of the catheter 51 in relation to the atheroma B and further to check the state of the atheroma B. The position of the catheter 51 with respect to the atheroma B can then be adjusted so as to allow a medical treatment. In this state, laser light such as YAG laser light is emitted from the top portion of the laser fiber 54 toward the atheroma B which is in turn is melted and removed thermally. Here, the laser illumination to the atheroma B is repeatedly performed under the condition of successively checking the melting state of the atheroma B, because the melting speed and melting state of the atheroma depends upon the laser illuminating power, laser illuminating time and the like.

Problems arise with such a conventional arrangement. Because the state of the atheroma B is checked through the endscope scanning operation during the laser medical treatment, difficulty is encountered in obtaining sufficient information of the atheroma B in the depth direction. Also, since the transparent flush agent (physiological brine) is injected several times through the injection hole 52 into the blood vessel A, there is the possibility that a large amount of the physiological brine is given with respect to the living body. In addition, if the laser illumination time is long, the laser light can penetrate into the atheroma B so as to damage a normal portion of the blood vessel A due to the laser energy. Moreover, the long laser illumination time can increase the temperature of the anatomy or tissue at the vicinity of the atheroma B. Accordingly, the extremely accurate management is required in terms of the laser illumination time and laser illumination power.

SUMMARY OF THE INVENTION

It is therefore an object of the present invention to provide a catheter type laser illuminating apparatus which is capable of checking, through the visual sensation, the relation between the laser light and the melting state of the atheroma in the depth direction, thereby easily and safely removing the atheroma.

A catheter type laser illuminating apparatus according to the present invention comprises a catheter arranged to be inserted into a blood vessel. The catheter is equipped with an ultrasonic transducer for transmitting and receiving an ultrasonic wave to generate an electric signal corresponding to the reception ultrasonic wave and further equipped with a laser transmission fiber for emitting the laser light. Also included in the illumination apparatus is a M-mode image producing section for producing an image representative of the dimension of the atheroma on the basis of the electric signal from the ultrasonic transducer. The M-mode image, being well known, is for displaying the movement of an object with passage of time, i.e., for displaying the shifting of luminance points (reflection objects) of the A-mode indication with passage of time. The image is displayed on a CRT in a corresponding relation to an illumination condition of the laser light to the atheroma which is at least one of an illumination time and an illumination power.

Another feature of this invention is to calculate the next illumination condition on the basis of the degree of the removal of the atheroma due to the previous illumination.

In accordance with the present invention, there is provided a system for acoustically inspecting a state of an object presented in a narrow place and thermally removing the object by illumination of laser light. The system comprises an elongated and hollow member arranged to allow insertion into the narrow place and laser illumination means. The laser illumination means include a laser transmission fiber one end of which extends through the inside of the elongated and hollow member up to a top or distal portion thereof so as to allow an opposed relation to the object; and laser generation means coupled to the other end of the laser transmission fiber means for generating laser light in accordance with a control signal representative of an illumination condition to be inputted from an external source. Thus, the generated laser light is emitted from the laser transmission fiber toward the object in response to the input of the control signal. The system further comprises ultrasonic inspection means which includes: ultrasonic transducer means provided at a top portion of the elongated and hollow member so as to allow an opposed relation to the object. The ultrasonic transducer means transmits an ultrasonic wave and receives reflection ultrasonic wave signals from the object to generate an electric signal corresponding to the reflected ultrasonic wave signals. An image producing means coupled to the ultrasonic transducer means produces an image representing a dimension of the object. The image producing means are also coupled to the control signal from the external source so that the produced image is displayed in a corresponding relation to the illumination condition.

In accordance with the present invention, there is further provided a system for acoustically inspecting a state of an object presented in a narrow place and thermally removing the object by illumination of laser light, the system comprising:

an elongated and hollow member arranged to allow insertion into the narrow place; ultrasonic inspection means including: ultrasonic transducer means provided at a top or distal portion of the elongated and hollow member so as to allow an opposed relation to the object, the ultrasonic transducer means being arranged so transmit an ultrasonic wave and receives reflected ultrasonic wave signals from the object to generate an electric signal corresponding to the reflected ultrasonic wave signals; and image producing means coupled to the ultrasonic transducer means so as to produce an image representing a dimension of the object and display the produced image on a screen, laser illumination means including: laser transmission fiber means one end of which extends through the inside of the elongated and hollow member up to a top portion thereof so as to allow an opposed relation to the object; calculation means coupled to the ultrasonic transducer means for calculating a condition for illuminating the object with laser light on the basis of the electric signal outputted from the ultrasonic transducer means; and laser generation means coupled to the other end of the laser transmission fiber means and further coupled to the calculation means for generating laser light in accordance with the calculated illumination condition, so that the generated laser light is emitted from the laser transmission fiber means toward the object under the calculated illumination condition.

BRIEF DESCRIPTION OF THE DRAWINGS

The objects and features of the present invention will become more readily apparent from the following detailed description of the preferred embodiments taken in conjunction with the accompany drawings in which.

DETAILED DESCRIPTION OF THE INVENTION

Figure 2:
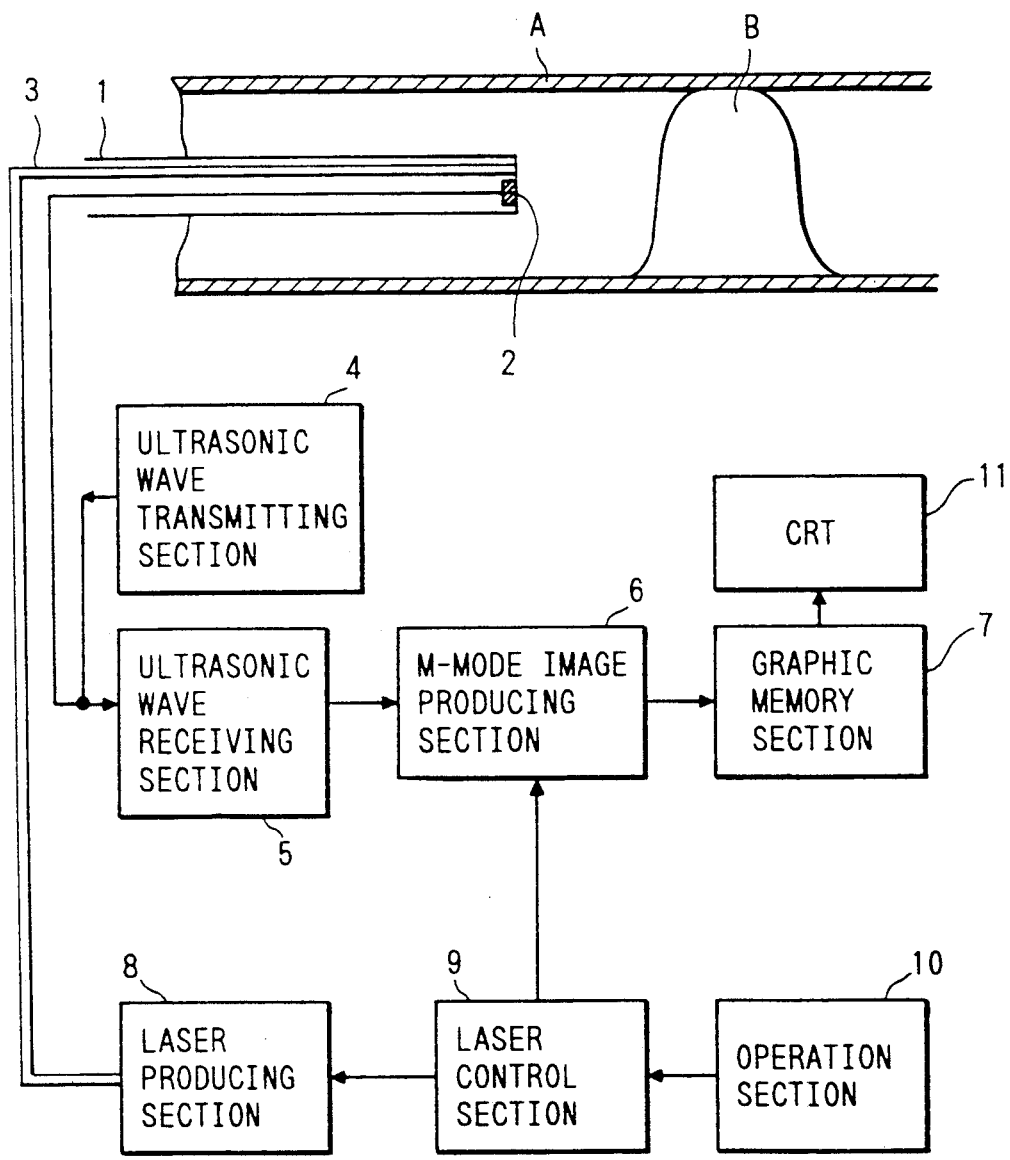
FIG. 2 is a block diagram showing an arrangement of a catheter type laser illumination apparatus according to a first embodiment of the present invention.

Referring now to FIG. 2, there is illustrated an arrangement of a catheter type laser illuminating apparatus according to an embodiment of the present invention. In FIG. 2, illustrated at numeral 1 is an elongated and hollow catheter which has at its distal portion an ultrasonic transducer 2 and which further has its inside a laser transmission fiber 3. The ultrasonic transducer 2 is coupled to an ultrasonic wave transmitting section 4 and further to an ultrasonic wave receiving section 5 which is composed of a preamplifier, for example. The ultrasonic wave receiving section 5 is coupled to an M-mode image producing section 6 which is in turn coupled to a graphic memory section 7, and the laser transmission fiber 3 is coupled to a laser producing section 8. Further, illustrated at numeral 9 is a laser control section which is coupled to the laser producing section 8 and further to the M-mode image producing section 6. Numeral 10 represents an operation section coupled to the laser control section 9, numeral 11 is a CRT (cathode ray tube) coupled to the graphic memory section 7, and characters A and B denote a blood vessel and an atheroma generated in the blood vessel A, respectively.

Figure 3A:
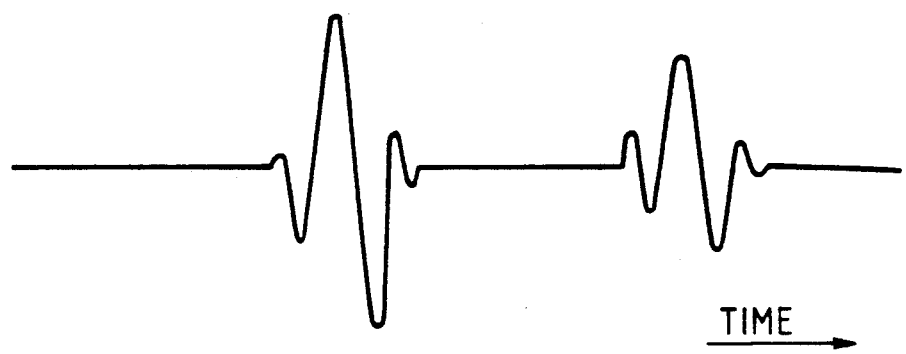
FIG. 3A shows a waveform of a reflection signal to be obtained by an ultrasonic transducer used in the FIG. 2 laser illumination apparatus.
Figure 3B:
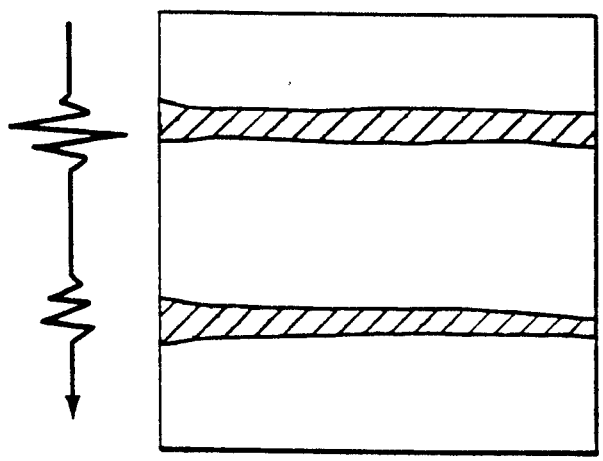
FIG. 3B illustrates a M-mode image produced on the basis of the reflection signal illustrated in FIG. 3A.

In operation, the catheter 1 is inserted into the blood vessel A so that the distal portion of the catheter 1 is moved up to the vicinity of the atheroma B. The ultrasonic wave transmitting section 4 supplies an electric pulse signal to the ultrasonic transducer 2 which converts the electric pulse signal into an ultrasonic wave signal for forward emission. The ultrasonic wave signal emitted from the ultrasonic transducer 2 propagates into the blood to advance toward the atheroma B, and, at the boundary portion between the blood and the ultrasonic transducer 2 side of the atheroma B, a portion of the ultrasonic wave signal is reflected because of occurrence of the acoustic impedance difference and another portion thereof penetrates or enters into the atheroma B. The reflected ultrasonic wave signal returns to the ultrasonic transducer 2. The penetrated ultrasonic wave signal propagates in the atheroma B, and a portion of the penetrated ultrasonic wave signal is reflected at the boundary portion between the opposite side of the atheroma B and the blood due to the occurrence of the acoustic impedance difference so as to return to the ultrasonic transducer 2 after passing through the atheroma B. The time difference between the two reflected wave signals allows detection of the length of the atheroma B in the depth direction. FIG. 3A schematically illustrates the two reflected wave signals. The two reflected wave signals from the atheroma B are respectively converted into electric signals in the ultrasonic transducer 2 which are in turn amplified in the ultrasonic wave receiving section 5 and supplied to the M-mode image producing section 6. In the M-mode image producing section 6 where an M-mode image is produced on the basis of the electric signals from the ultrasonic transducer 2. The M-mode image produced, together with time information, is written in the graphic memory section 7 and displayed by the CRT 11. FIG. 3B illustrates the M-mode image corresponding to the reflected wave signals shown in FIG. 3A.

In response to the production of the M-mode image of the atheroma B, the laser producing section 8 generates a laser light which is in turn emitted through the laser transmission fiber 3 from the top portion of the catheter 1 so that the atheroma B is illuminated with the laser light for a predetermined time T1. At this time, the laser illumination time and the illumination power (intensity) are controlled by the laser control section 9 in accordance with the instructions made through the operation section 10. The information relating to the laser illumination time and illumination power is also supplied through the laser control section 9 to the M-mode image producing section 6. The long laser illumination time causes the laser light to penetrate the atheroma B which may damage a normal anatomy ahead of the atheroma B due to the laser energy or increase in the temperature. Thus, the laser illumination time must be set so as not to damage the normal anatomy. Particularly, the initial illumination condition such as the illumination time and illumination power, must be adequately determined to be in a predetermined range that cannot penetrate the atheroma B at a time.

After the laser illumination for the predetermined time T1, the M-mode image is again produced by a procedure similar to the above-described process. At this time, the M-mode image will show the fact that the dimension of the atheroma B is reduced in correspondence with the laser illumination time T1.

In displaying the current M-mode image on the CRT 11, the previous M-mode image before the laser illumination (first laser illumination), being stored in the M-mode image producing section 6, is also displayed on a different area of the same CRT 11. Here, the indication width of the M-mode image to be displayed on the CRT 11 after the first laser illumination is arranged to correspond to the laser illumination time T1. As described above, the information relating to the laser illumination time T1 is supplied from the laser control section 9 to the M-mode image producing section 6. Secondly, the second illumination is performed for a laser illumination time T2 and a similar ultrasonic scanning is then effected so as to produce a new M-mode image to check the melted state of the atheroma B. This M-mode image is displayed on the CRT 11 (a portion different from the portion for displaying the M-mode image after the first laser illumination) so as to have a width corresponding to the illumination time T2.

Figure 4:
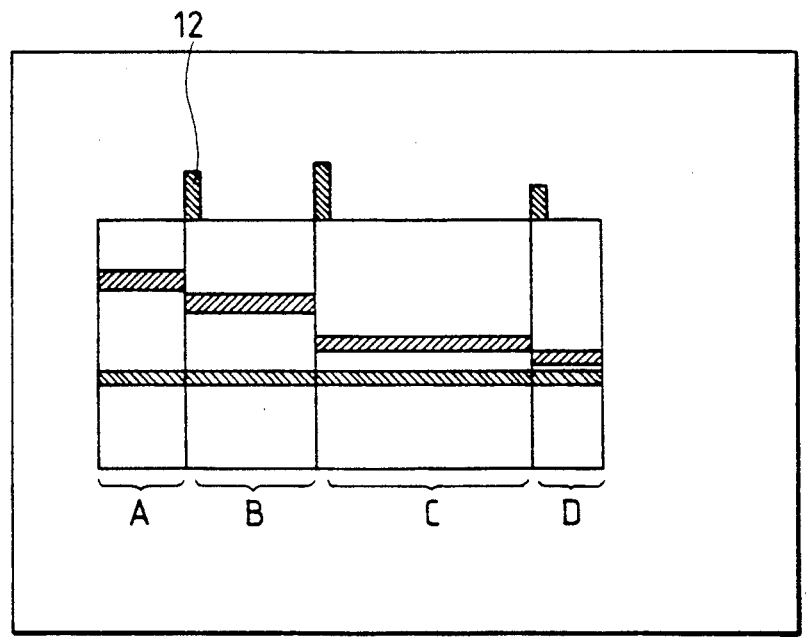
FIGS. 4 and 5 are illustrations of successive M-mode images to be obtained in accordance with the FIG. 2 laser illumination apparatus.

Let it be assumed that the first to third laser illumination time periods are taken to be T1 to T3 and the relation between the time periods T1 to T3 is T2>T1>T3. In this case, the M-mode images are displayed on the CRT 11 as illustrated in FIG. 4. In FIG. 4, the area A shows the M-mode image before the laser illumination, the area B shows the M-mode image after the first laser illumination, and the areas C and D respectively show the M-mode images after the second and third laser illuminations. Here, the widths of the areas B to D respectively correspond to the laser illumination time periods, T1, T2, T3. This display system allows simultaneously checking the laser illumination time and the melted state of the atheroma B through the visual sensation. By using this information, the user can easily obtain the depth-direction information of the atheroma B and accurately set the subsequent laser illumination time through the operation section 10. In FIG. 4, numeral 12 represents an illumination power bar whose length corresponds to the laser illumination power. This can provide the further information for the more accurate medical treatment. After a through-hole is formed in the atheroma B by the laser illuminating operations, as well as in the conventional technique, the catheter 1 may be inserted into the formed through-hole so that a balloon (not shown) is expanded so as to enlarge the blood vessel A.

Figure 5:
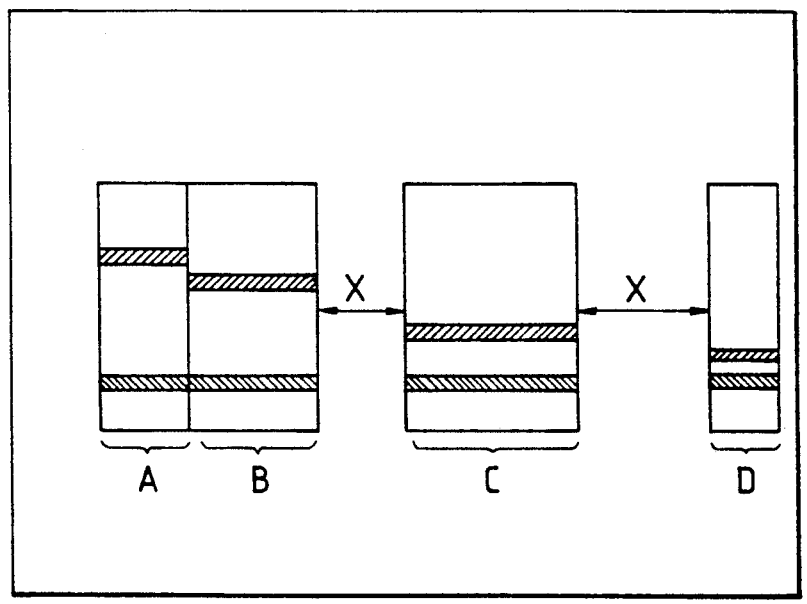

Although in the above-described embodiment the laser illuminating operations are successively performed, it is also appropriate that the laser illuminating operations are intermittently performed at a predetermined time interval. In this case, the space X corresponding to the predetermined time interval can further be displayed on the CRT as illustrated in FIG. 5.

The M-mode image is displayed on the CRT 11 in correspondence with only the laser illumination time in the case that the illumination power is constant or displayed thereon in correspondence with only the illumination power in the case the illumination time is constant. It is also appropriate that the M-mode image is displayed thereon in correspondence with the product of the illumination time and the illumination power, i.e., the illumination energy.

Figure 1:
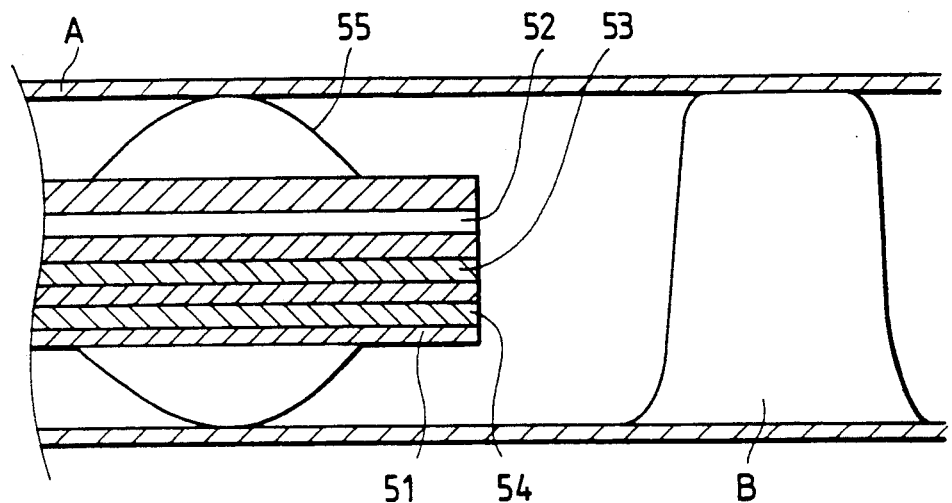
FIG. 1 is a cross-sectional view showing an arrangement of a conventional catheter type laser illumination apparatus.
Figure 7A:
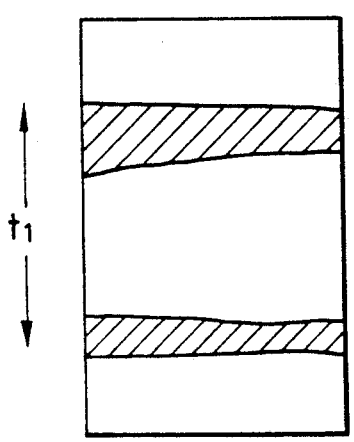
FIGS. 7A and 7B are illustrations of M-mode images to be obtained by the FIG. 6 laser illumination apparatus.
Figure 7B:
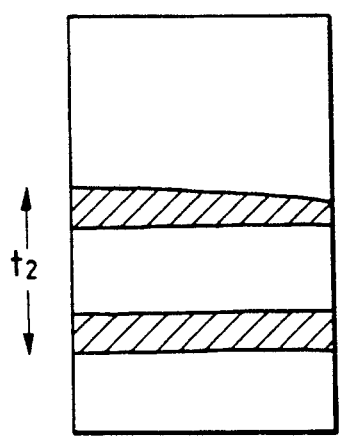
Figure 6:
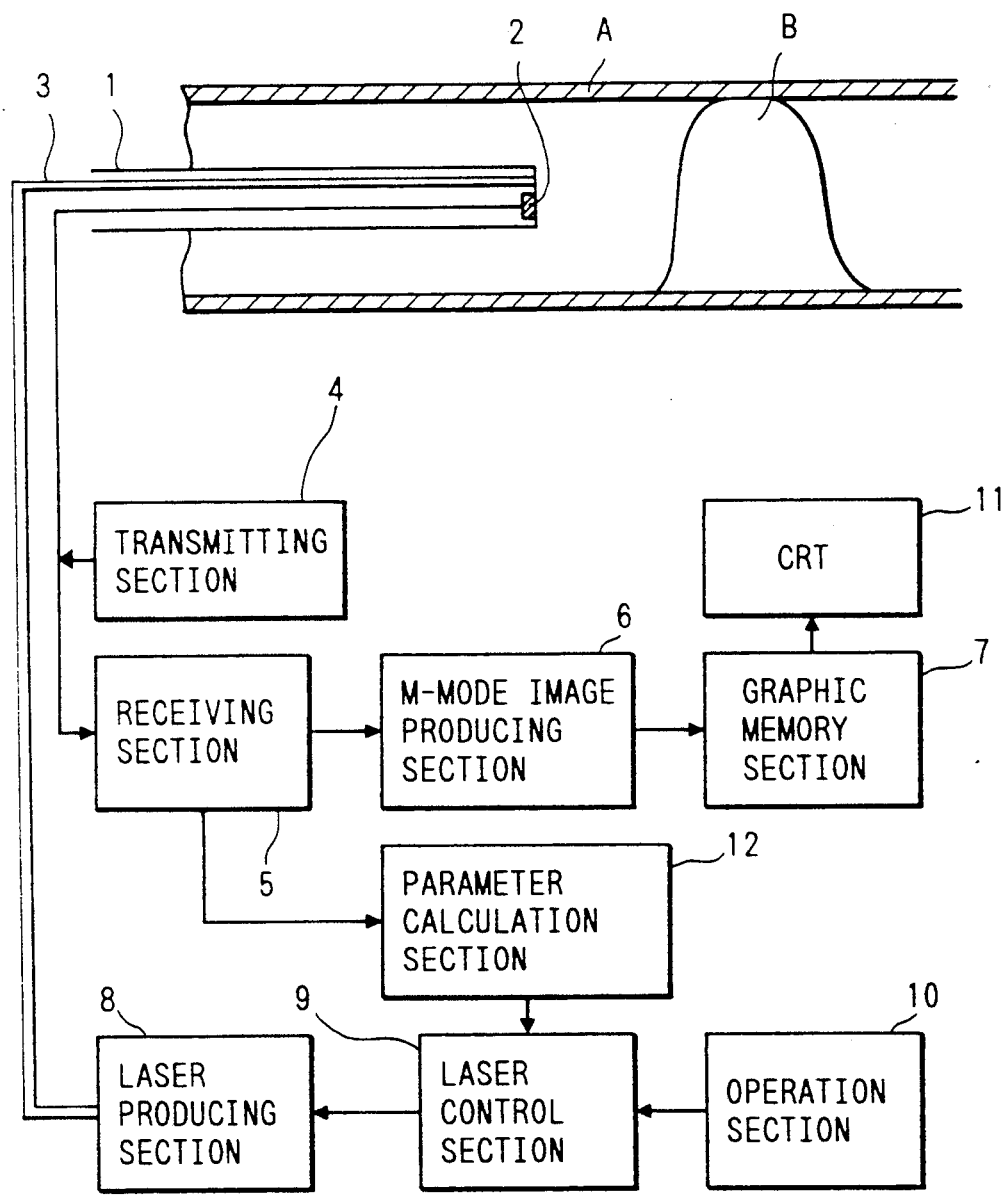
FIG. 6 is a block diagram showing an arrangement of a catheter type laser illuminating apparatus according to a second embodiment of this invention.

A second embodiment of this invention will be described hereinbelow with reference to FIG. 6 where parts corresponding to those in FIG. 2 are marked with the same numerals and characters, and the description thereof will be omitted for brevity. The feature of the second embodiment is to automatically calculate the laser illumination condition such as the illumination time and illumination power. In FIG. 6, the difference from the apparatus in FIG. 2 is that there is further provided a parameter calculation section 12 which is responsive to the output signal of the ultrasonic wave receiving section 5. The parameter calculation section 12 calculates the length of the atheroma B on the basis of the output of the ultrasonic wave receiving section 5 after the first laser illumination so as to calculate an adequate condition for the second laser illumination. This calculation result is supplied to the laser control section 9 which in turn controls the laser producing section 8 so as to generate laser light corresponding to the calculated laser illumination condition. For determining a laser illumination condition, such as the illumination time and illumination power, the second laser illumination condition must be determined by taking into account the melting degree of the atheroma B due to the first laser illumination so that the laser light in the second illumination does not penetrate the remaining atheroma B. For example, if as illustrated in FIGS. 7A and 7B, the length of the atheroma B before the first laser illumination is t1 and the length thereof after the first illumination is t2 and the time of the first illumination is T1, the next laser illumination time T2 for reducing the length t2 to the half can be calculated in accordance with the following equation under the consideration that the relation between the melting speed of the atheroma b and the illumination time is linear.

$$T1:T2 = (t1-t2):t2/2$$

$$T2 = \frac{t2 \times T1}{2 \times (t1 - t2)}$$

The calculated illumination time T2 is supplied as a parameter of the laser illumination to the laser control section 9. The laser control section 9 outputs a control signal on the basis of the parameter supplied. The laser producing section 8 generates laser light for the time T2 in accordance with the control signal from the laser control section 9.

It should be understood that the foregoing relates to only preferred embodiments of the present invention, and that it is intended to cover all changes and modifications of the embodiments of the invention herein used for the purposes of the disclosure, which do not constitute departures from the spirit and scope of the invention. For example, although in the above-described embodiments the laser illumination is performed in accordance with the so-called laser illuminating and melting system where the atheroma is directly illuminated and melted with the laser light, this invention is applicable to the so-called metal chip system where a metal chip is illuminated and heated with the laser light and the atheroma is indirectly removed thermally through the metal chip.

What is claimed is:

1. A catheter type laser illuminating apparatus comprising:
    a catheter arranged to be inserted into a blood vessel;
    an ultrasonic transducer provided at a distal portion of said catheter for transmitting an ultrasonic wave toward an object in said blood vessel and receiving a reflected wave from said object to generate a signal corresponding to the received reflected wave;

a laser transmission fiber inserted in said catheter;

laser producing means for producing laser light which is emitted through said laser transmission fiber to iluminate an object in said blood vessel;

laser control means for outputting a laser control signal to said laser producing means so that said laser producing means produces said laser light in accordance with said laser control signal; and display means coupled to said ultrasonic transducer and said laser control means for producing an image based on said signal generated by said ultrasonic transducer, the image being two-dimensionally displayed to have a width corresponding to a time period of illumination of said laser light taken in accordance with said laser control signal.

2. A catheter type laser illuminating apparatus as claimed in claim 1, further comprising:

parameter calculation means coupled to said ultrasonic transducer to be responsive to the signal corresponding to the received reflected wave for calculating a laser illuminating condition in accordance with the following equation, so as to control said laser control means so that said laser light from said laser producing means is emitted in accordance with the calculated laser illuminating condition:

$$T1:T2=(t1-t2):t2/2$$

where t1 represents a length of said object before a first illumination of said laser light to said object, t2 designates a length of said object after the first ilumination, T1 denotes a time period taken for the first illumination, and T2 depicts a time period to be taken for a succeeding illumination to further reduce the length t2 of said object.

3. A catheter type laser illumination apparatus as claimed in claim 1, wherein said display means further displays an image corresponding to an illumination power of said laser light.

4. A system for acoustically inspecting a state of an object presented in a narrow place and thermally removing said object by ilumination of laser light, said system comprising:

an elongated and hollow member arranged to allow insertion into said narrow place;

laser transmission fiber means one end of which extends through the inside of said elongated and hollow member to a distal end thereof so as to face toward said object;

laser generation means coupled to another end of said laser transmission fiber means for generating laser light in accordance with a control signal representative of an illumination condition to be inputted from an external source, so that the generated laser light is emitted from said laser transmission fiber means toward said object in response to the input of said control signal;

ultrasonic transducer means, at said distal end of said elongated and hollow member so as to face toward said object, for transmitting an ultrasonic wave and receiving ultrasonic wave signals reflected from said object to generate an electric signal corresponding to said reflected ultrasonic wave signals; and image producing means coupled to said ultrasonic transducer means, for producing and displaying an image representing a dimension of said object, said image producing means being also coupled to the conrol signal from the external source so that the image is displayed to be in a corresponding relation to said illumination condition.

5. A system as claimed in claim 4, wherein said laser generation means operates responsive to said control signal so as to define said illumination condition as at least one of an illumination time period and an illumination lintensity of the laser light.

6. A system acoustically inspecting a state of an object presented in a narrow place and thermally removing said object by illumination of laser light, said system comprising:

an elongated and hollow member arranged to allow insertion into said narrow place;

ultrasonic transducer means provided at a top portion of said elongated and hollow member so as to face toward said object for transmitting an ultrasonic wave and receiving an ultrasonic wave reflected from said object to generate an electric signal corresponding to the reflected ultrasonic wave; and image producing means coupled to said ultrasonic transducer means so as to produce an image representing a dimension of said object and display the produced image on a screen, laser transmission fiber means one end of which extends through said elongated and hollow member to a distal portion thereof so as to face toward said object;

calculation means coupled to said ultrasonic transducer means for calculating a condition for illuminating said object with laser light based on the electric signal corresponding to the reflected ultrasonic wave; and laser generation means coupled to another end of said laser transmission fiber means and further coupled to said calculation means for generating laser light in accordance with the calculated condition for illuminating, so that the generated laser light is emitted from said laser transmission fiber means toward said object.

7. A system as claimed in claim 6, wherein said calculation means calculates at least one of an illumination time period and an illumination intensity of the laser light as the calculated condition for illuminating.

8. A system as claimed in claim 6, wherein said calculation means calculates the condition for illuminating based on a degree of removal of said object due to an illumination condition which degree is detected by the electric signal corresponding to the reflected ultrasonic wave.

* * * * *